United States Patent [19]

Cook

[11] Patent Number: 5,339,802
[45] Date of Patent: Aug. 23, 1994

[54] ENDOSCOPIC RETRACTOR

[76] Inventor: Richard G. Cook, 9217 Berkshire Cir., Chattanooga, Tenn. 37241

[21] Appl. No.: 963,895

[22] Filed: Oct. 19, 1992

[51] Int. Cl.⁵ ............................................. A61B 17/02
[52] U.S. Cl. ..................................... 128/20; 128/17; 606/198
[58] Field of Search ............................. 128/17–20, 128/3, 8; 606/190, 191, 197, 198, 205–208; 604/104–109; 294/97

[56] References Cited

U.S. PATENT DOCUMENTS

| | | | |
|---|---|---|---|
| 3,132,890 | 5/1964 | Beaudet | 294/97 |
| 4,838,595 | 6/1989 | Spillar | 294/97 X |
| 5,152,279 | 10/1992 | Wilk | 128/17 |
| 5,195,505 | 3/1993 | Josefsen | 128/20 |
| 5,199,419 | 4/1993 | Remiszewski et al. | 128/20 |

FOREIGN PATENT DOCUMENTS

| | | | |
|---|---|---|---|
| 736949 | 5/1980 | U.S.S.R. | 606/198 |
| 990220 | 1/1983 | U.S.S.R. | 128/20 |
| 1577769 | 7/1990 | U.S.S.R. | 128/20 |

*Primary Examiner*—Richard J. Apley
*Assistant Examiner*—Donna L. Maraglio
*Attorney, Agent, or Firm*—Mark J. Patterson; Edward D. Lanquist, Jr.; I. C. Waddey, Jr.

[57] ABSTRACT

The present invention discloses an endoscopic retractor for use in minimal invasive surgery. A retractor blade is pivotally attached to an elongated hollow cylinder. An elongated shaft slides and rotates within the cylinder. At one end of the shaft is a handle. The other end includes a locking surface which bears against the blade. The blade can be positioned for movement of the retractor through a cannula, then moved into a closed position for use during the procedure.

4 Claims, 6 Drawing Sheets

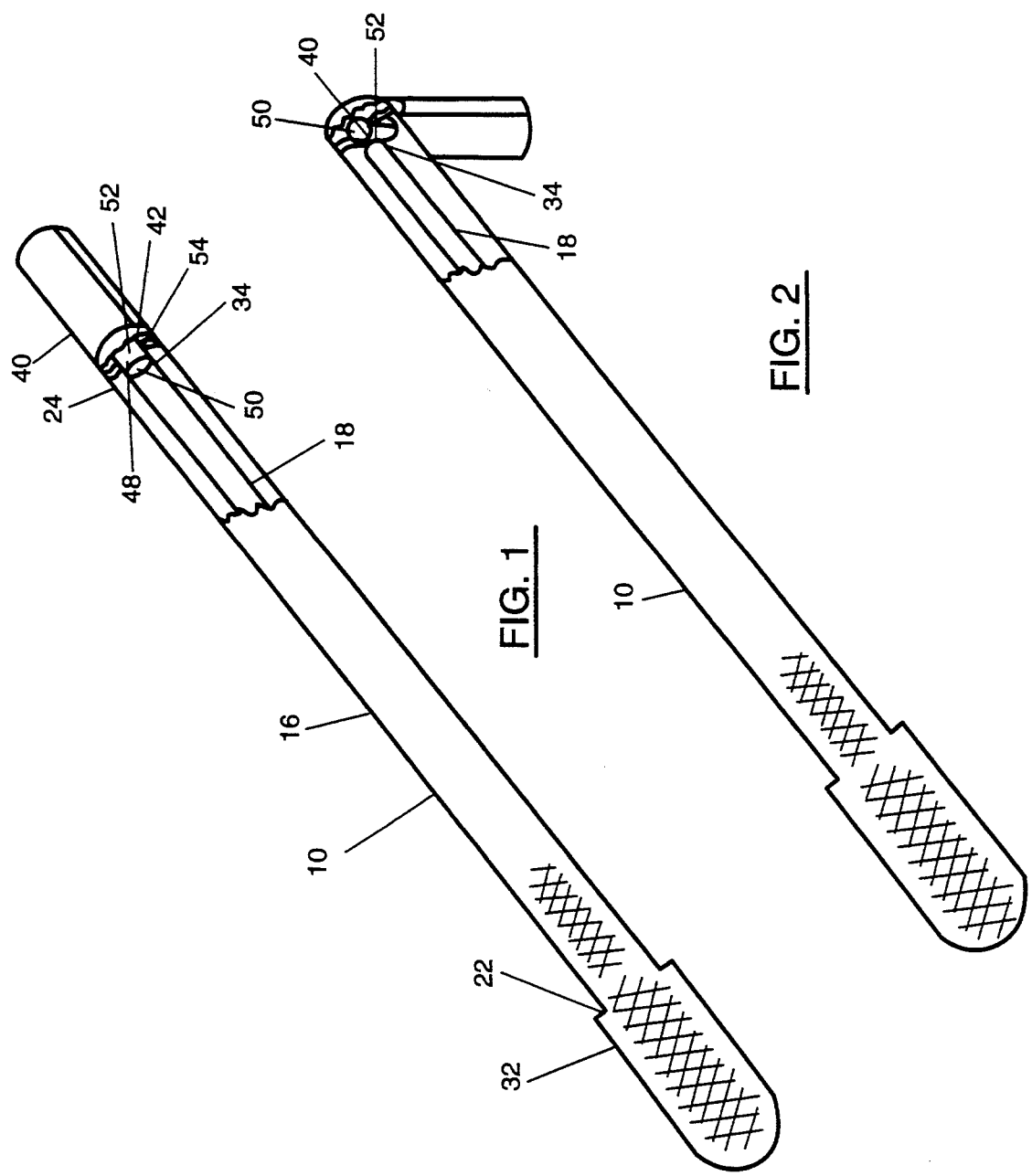

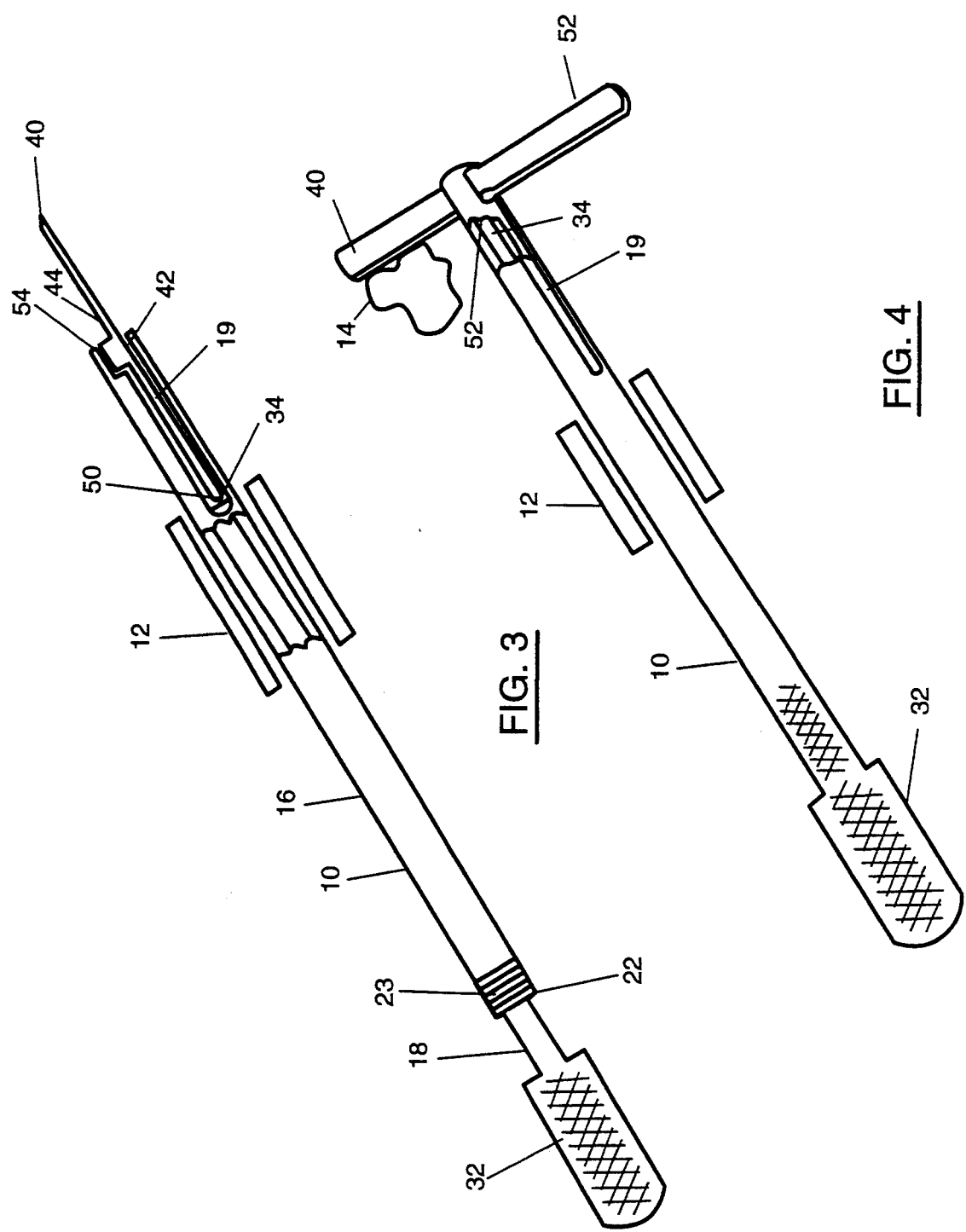

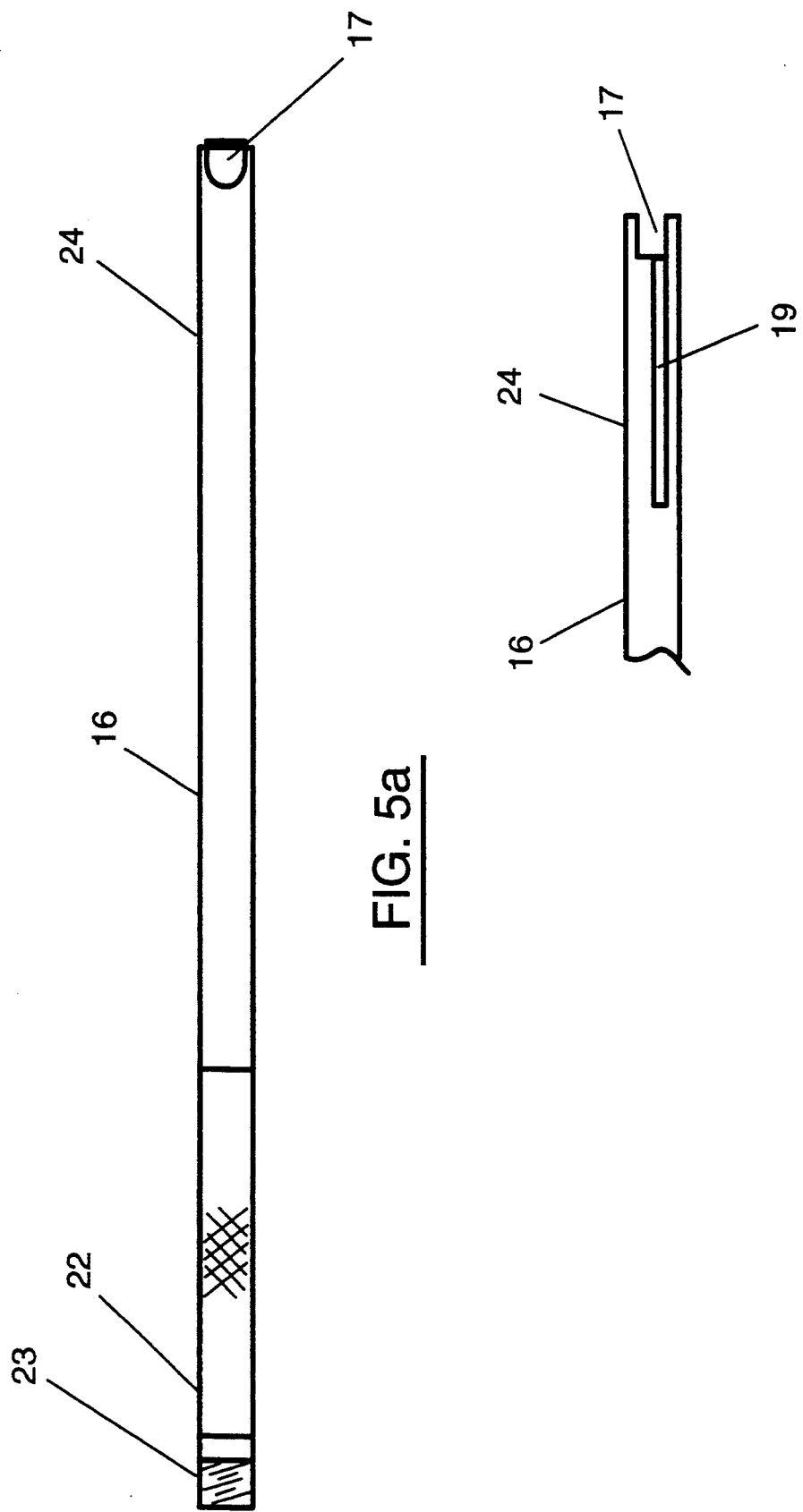

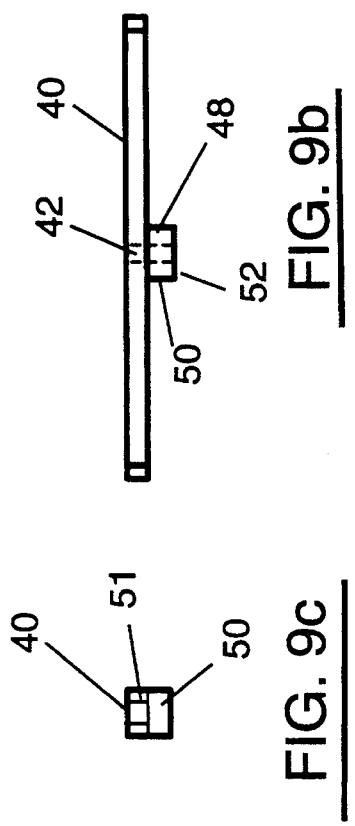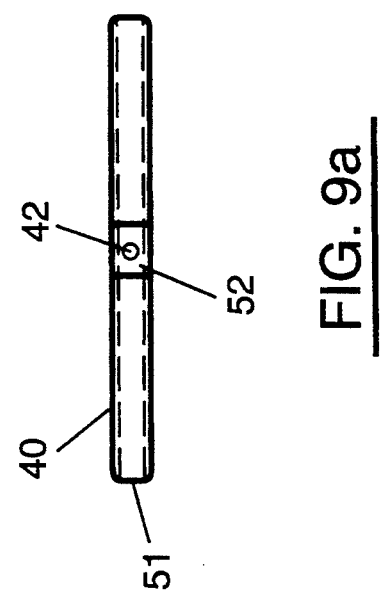

ENDOSCOPIC RETRACTOR

BACKGROUND OF THE INVENTION

The present invention relates generally to surgical instruments and more particularly to a surgical retractor used in laparoscopic surgery for manipulating and holding into position organs and structures to make various surgical procedures possible and more easily performed.

It will be appreciated by those skilled in the art that tools are needed to manipulate and secure organs and other body structures during surgical procedures. Such tools, commonly known in the art as retractors, have proven very useful for many years and are use extensively for open surgical procedures such as bowel resections. It will further be appreciated by those skilled in the art that the popularity of minimal invasive or laparoscopic surgery has risen, with many procedures previously performed through open and fully exposed surgical fields now being done by use of endoscopes and instruments manipulated through small diameter cannulas placed into the body. Even with this rise in the number of laparoscopic surgeries, retractors which can perform the traditional functions of organ and tissue manipulation are still needed.

Unfortunately, prior art retractors consisted of handles rigidly attached to variously shaped blades. These blades were designed to be slipped behind the lung, for example, so that it could be raised or otherwise manipulated to allow a procedure to be performed on the posterior of the lung which would not have been possible otherwise. With such designs, retractors could not be effectively used in connection with laparoscopic procedures.

What is needed, then, is a retractor for use in connection with laparoscopic procedures, including the ability to be passed through a small diameter cannula and into the desired body cavity. This retractor must also be easy to use and manufacture. Such a device is presently lacking in the prior art.

SUMMARY OF THE INVENTION

The present invention discloses a surgical retractor specifically adapted for use in connection with laparoscopic surgery. The retractor has an elongated hollow cylinder which is open at each end, thereby defining an elongated internal cavity. The lower end of the cylinder includes means to pivotally attach a retractor blade. An elongated shaft is slidably received by the cavity in the cylinder. At one end of the shaft is a handle. The other end of the shaft is a blunt, flat surface which bears against a segment of the retractor blade to lock it into position during use. The handle is used to slide the shaft within the cylinder and to temporarily secure the shaft into position by threading onto the outer surface of the upper end of the cylinder.

When the shaft handle is not secured to the cylinder, and the shaft partially removed, the blade can be pivoted in an open position of longitudinal alignment with the cylinder and then fixed in that position by re-securing the handle. This allows the retractor to be placed into the body cavity through a cannula of small diameter. After insertion, the handle can again be loosened, the blade pivoted into a laterally extended closed position for use, and fixed there by re-tightening of the handle, causing the lower end of the shaft to bear against the blade. Accordingly, one object of the present invention is to provide a retractor which can be used through a cannula in connection with minimally invasive surgical procedures. Still a further object of the present invention is to provide a retractor which is simple and inexpensive to make. Still a further object of the present invention is to provide a device which is easy to use.

BRIEF DESCRIPTION OF THE DRAWINGS

FIG. 1 is a side cut-away view of a right-angle blade embodiment of the retractor of the present invention, with the handle in an open position for entry into a cannula.

FIG. 2 is a side cut-away view of the retractor of FIG. 1, with the blade in a closed position extended for use within the body cavity.

FIG. 3 is a side cut-away view of a second embodiment of the retractor of the present invention in which the blade is of a "T" configuration, in an open position.

FIG. 4 is a side cut-away view of the T-blade embodiment of FIG. 3, in a closed position.

FIG. 5a is a side view of the cylinder of the right-angle blade retractor of the present invention.

FIG. 5b is a partial side view showing the lower end of the cylinder of the T-blade retractor.

FIGS. 9a,b, and c are top, side, and end views of the T-blade of the present invention.

DETAILED DESCRIPTION OF THE PREFERRED EMBODIMENT

Figure 6:
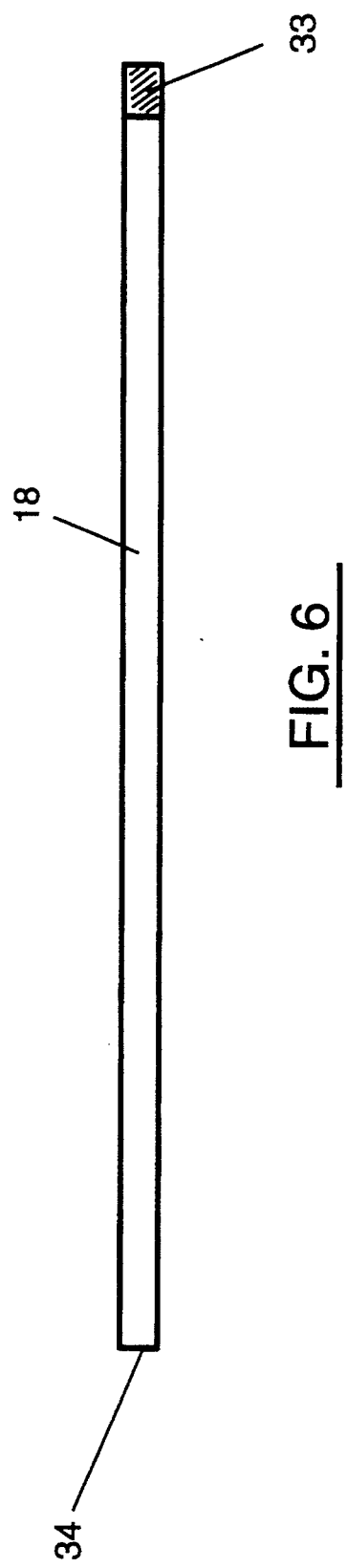
FIG. 6 is a side view of the shaft of both embodiments of the present invention, with the handle removed.

Referring now to FIG. 1 there is shown generally at 10 one embodiment of the endoscopic retractor of the present invention. Retractor 10 generally includes a hollow elongated cylinder 16 which is open at both upper end 22 and lower 24, thereby defining an internal cavity running the entire length of cylinder 16. Elongated shaft 18, which must move through and rotate within cylinder 16, has handle 32 and lock end 34. As seen on FIGS. 3 and 5a, the outer surface at the upper end 22 of cylinder 16 incorporates threaded area 23 so that cylinder 16 can be releasably attached to handle 32 of elongated shaft 18. In the preferred embodiment, both cylinder 16 and shaft 18 are made of a conventional surgical steel or other suitably rigid and biocompatible material.

Figure 8B:
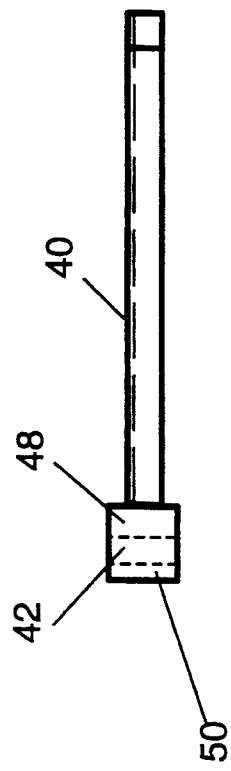
FIGS. 8a,b, and c are top, side, and end views respectively of the right-angle blade.
Figure 8A:
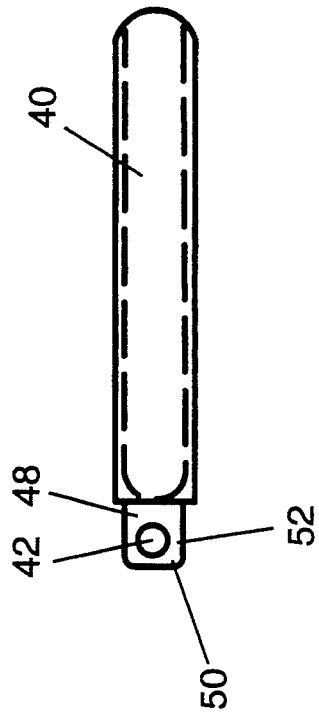
Figure 8C:
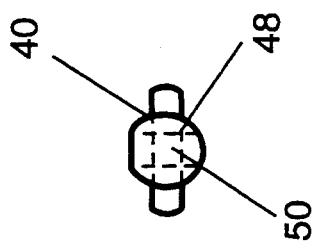

Looking now at FIGS. 1, 2, and 5a, at lower end 24 of cylinder 16 are means to pivotally attach blade 40, in this embodiment a right-angle retractor blade as shown on FIG. 8. An approximately u-shaped aperture 17 is formed at lower end 24 of cylinder 16 to accommodate movement of blade 40 from the open or entry position shown on FIG. 1 to the closed position of FIG. 2. Attached across the internal cavity and to the internal walls of cylinder 16 at lower end 24, and substantially aligned with aperture 17, is pivot pin 54. As seen best on FIG. 8, right-angle blade 40 includes a locking plate 48 through which pivot hole 42 extends and which rotatably receives pin 54.

In operation, lock plate 48 uses open face 50 and closed face 52. Elongated shaft 18 is sized such that when handle 32 fully engages threaded area 23 of cylinder 16 at upper end 22, the flat surface of lock end 34 will contact and bear against lock plate 48 to lock blade 40 into position. When blade 40 is pivoted around pin 54 into the open position as shown on FIG. 1, lock end 34 of shaft 18 will be in contact with open face 50 of plate 48. So positioned, retractor 10 can easily be placed into the body cavity through a conventional laparoscopic cannula (12 on FIG. 4). After placement of retractor 10 proximate to the organ or tissue to be retracted, handle 32 of shaft 18 is backed off of threaded area 23, causing lock end 34 of shaft 18 to separate from open face 50 of lock plate 48. Blade 40 can now be manipulated by force of gravity and by contact with adjacent tissues, to pivot around pin 54 to laterally extend away from cylinder 16 through aperture 17 into the closed position shown in FIG. 2. To secure blade 40 into this closed position, handle 32 is once again tightened down, causing lock end 34 to bear against closed face 52 of lock plate 48.

Referring now to FIGS. 3, 4, 5b, and 9 there is shown generally at 10 a second embodiment of the retractor of the present invention in which blade 40 is substantially T-shaped. In this embodiment, a second, lengthened aperture 19 is placed into the surface of cylinder 16 adjacent aperture 17. This will permit rotation about pivot pin 54 of a T-shaped blade 40 as shown in FIG. 9, with one segment of blade 40 resting within aperture 19 as shown in FIG. 3. In this embodiment, locking plate 48 is centrally located within blade 40. As described above, pin 54 is rotatably engaged by hole 42, and lock end 34 of shaft 18 alternatively bears against open face 50 of plate 48 as shown in FIG. 3 or closed face 52 as shown on FIG. 4. If preferred, or if there is inadequate space within cylinder 16 to accommodate shaft 18 and blade 40 in parallel, shaft 18 can be further withdrawn from within cylinder 16 so that lock end 34 bears against alternate open face 51 shown on FIG. 9. In the closed position, blade 40 can be used to retract an organ (14 on FIG. 4) such as a lobe of the lung or liver. In use, retractor 10 is manipulated while entered into the body cavity through cannula 12.

Figure 7B:
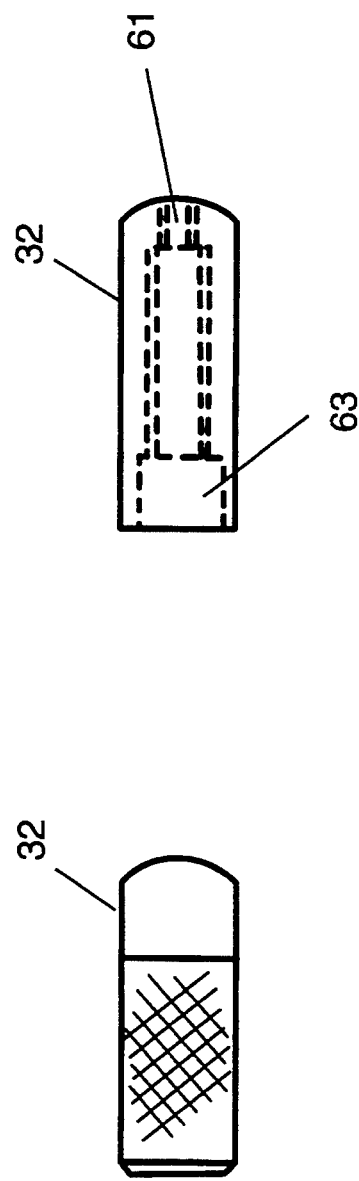
FIGS. 7a and b are side and side phantom views of the handle component of the retractor used in both embodiments of the present invention.
Figure 7A:
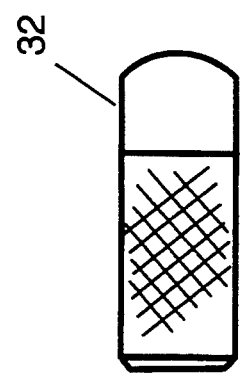

Referring now to FIGS. 6 and 7, elongated shaft 18 has threaded end surface 33 and lock end 34. Handle 32 has a first internal chamber 61 which itself is internally threaded to receive threaded end surface 33 of shaft 18. A second internal chamber 63 in handle 32 is internally threaded to engage threaded area 23 of cylinder 16.

For purposes of elevating or repositioning the lung, for example, it is known that a right-angle blade 40 of approximately twenty millimeters to sixty millimeters in length, depending upon the procedure, is required. In addition, it is known that certain procedures require a T-type structure (as shown in FIGS. 3 and 4) of length forty millimeters to one hundred twenty millimeters depending upon the procedure. To adapt to prior art cannulas, the outside diameter of cylinder 16 should be approximately five to ten millimeters. Obviously, the maximum dimensions of blade 40 must be chosen so that they conform both to the internal diameter of cannula 12 and to the size of apertures 17 and 19. Preferably the outside diameter of handle 32 is large enough to accommodate ease of manipulation and to prevent passage of retractor 10 completely through cannula 12.

Thus, although there have been described particular embodiments of the present invention of a new and useful endoscopic retractor, it is not intended that such references be construed as limitations upon the scope of this invention except as set forth in the following claims. Further, although there have been described certain dimensions used in the preferred embodiment, it is not intended that such dimensions be construed as limitations upon the scope of this invention except as set forth in the following claims.

What I claim is:

1. An endoscopic retractor comprising:
   a. an elongated cylinder having a cavity extending from an upper end through a lower end of said cylinder and a first aperture formed in the surface of said cylinder at said lower end;
   b. a pivot pin mounted transversely across said cavity at said lower end of said cylinder, said pivot pin substantially aligned with said first aperture;
   c. a blade pivotally attached to said pivot pin, said blade freely moveable by gravity to an open position extending from and longitudinally aligned with said cylinder and to a closed position extending laterally from said cylinder through said first aperture; and
   d. an elongated shaft slidably and rotatably received by said cavity, said elongated shaft including a handle and a lock end for locking said blade in said open and closed positions by moving said lock end of said shaft against said blade.

2. The retractor of claim 1 further comprising a second aperture formed in the surface of said cylinder adjacent said first aperture, said blade freely movable by gravity through said second aperture to said closed position.

3. The retractor of claim 2 wherein said blade is T-shaped and said second aperture is lengthened to accommodate a segment of said blade, whereby when said blade is moved to said open position, one segment of said blade is positioned within said second aperture in substantial alignment with said cylinder, and wherein said blade is moveable through said second aperture to said closed position in which said blade extends laterally from said first aperture.

4. The retractor of either of claims 1, 2, or 3 wherein said handle removably engages said upper end of said cylinder when said blade is locked in said closed position.

* * * * *